US00PP37613P2

(12) United States Plant Patent
Liang

(10) Patent No.: US PP37,613 P2
(45) Date of Patent: Aug. 18, 2026

(54) ***MONSTERA* PLANT NAMED 'LONGPRIDEMO01'**

(50) Latin Name: *Monstera deliciosa*
Varietal Denomination: LONGPRIDEMO01

(71) Applicant: Long Pride Biotechnology Co., Ltd, Gaoshu Township (TW)

(72) Inventor: Jui-Fang Liang, Gaoshu Township (TW)

(73) Assignee: Long Pride Biotechnology Co., LTD (TW)

( * ) Notice: Subject to any disclaimer, the term of this patent is extended or adjusted under 35 U.S.C. 154(b) by 0 days.

(21) Appl. No.: 19/442,340

(22) Filed: Jan. 7, 2026

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP36,063 P2 * 8/2024 Hung ..... A01H 6/10
Plt./373

* cited by examiner

*Primary Examiner* — Susan Mccormick Ewoldt
*Assistant Examiner* — Zachariah Allan Kay

(57) ABSTRACT

A new and distinct cultivar of *Monstera* plant named 'LONGPRIDEMO01' is disclosed, characterized by striking neon-green colored with a glossy surface. Foliage is deeply lobed with well-defined cuts. Plants are fast growing, with an 8-inch pot ready to sell in 6 months. The new cultivar is a *Monstera* normally used for ornamental purposes.

1 Drawing Sheet

Latin name of the genus and species: *Monstera deliciosa*.
Cultivar denomination: 'LONGPRIDEMO01'.

BACKGROUND OF THE INVENTION

The new *Monstera* cultivar is the result of a naturally occurring whole plant mutation of the unpatented *Monstera deliciosa* 'Aurea'. The new cultivar was selected among a population of the parent plant which had been propagated by tissue culture. *Monstera* 'LONGPRIDEMO01' was found and selected by the inventor in a nursery in Kaohsiung, Taiwan in March of 2024.

Asexual reproduction of the new cultivar has been performed by both vegetative micro-cuttings and tissue culture. Asexual reproduction was first performed at a nursery in Pingtung County, Taiwan in June of 2024 using vegetative micro-cuttings. This propagation and subsequent propagation have shown that the unique features of this cultivar are stable and reproduced true to type in multiple successive generations.

SUMMARY OF THE INVENTION

The cultivar 'LONGPRIDEMO01' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LONGPRIDEMO01' These characteristics in combination distinguish 'LONGPRIDEMO01' as a new and distinct *Monstera* cultivar:

1. Large, mature leaves with striking neon-green color and a glossy surface.
2. Deeply lobed and well-defined leaf cuts
3. Fast-growing, able to finish an 8-inch pot size within 6 months.
4. Horizontal spreading growth habit, forming a wide canopy.
5. Ideal for 8" to 12" pots, suitable for both indoor and greenhouse display.

PARENT COMPARISON

Plants of the new cultivar *Monstera* 'LONGPRIDEMO01' are similar to plants of *Monstera* 'Aurea' in most horticultural characteristics; however, plants of the new cultivar 'LONGPRIDEMO01' differ in the following:

1. Leaves retain a neon lime or lemon-yellow tone and tend to maintain their bright coloration longer than 'Aurea'.
2. The leaves are uniform neon lime or lemon-green, with consistent color across the blade; they do not show variegation like 'Aurea'.
3. Leaves are heart-shaped and often develop fenestrations a few weeks earlier than 'Aurea'.
4. Petiole color is frequently bright lime-green or yellow-green, consistent with leaf color; petiole color of 'Aurea' is green.
5. The leaves are uniform neon lime or lemon-green, with consistent color across the blade. Does not show variegation as may be seen in 'Aurea'.

COMMERCIAL COMPARISONS

The new cultivar is similar to *Monstera* 'Thai Constellation', unpatented iN most horticultural characteristics; however, plants of the new cultivar 'LONGPRIDEMO01' differ in the following:

1. The new cultivar has bright neon lime or lemon-yellow leaves, whereas 'Thai Constellation' has solid medium to dark green leaves.
2. Leaves of the new cultivar are heart-shaped and develop fenestrations slightly earlier compared to 'Thai Constellation'.
3. The new cultivar is bushier with a more horizontal leaf orientation, while 'Thai Constellation' grows upright and climbing.
4. Petioles of the new cultivar are thinner and brightly colored, whereas 'Thai Constellation' petioles are thicker and green.
5. Leaves of the new cultivar are uniformly neon lime or lemon-green across the blade and do not show variegation, unlike 'Thai Constellation'.

The new cultivar is similar to *Monstera* 'HUTAMT41', U.S. Plant Pat. No. 36,063 iN most horticultural characteristics; however, plants of the new cultivar 'LONGPRIDEMO01' differ in the following:

1. The new cultivar has bright neon lime or lemon-yellow leaves, whereas 'HUTAMT41' has solid medium to dark green leaves.
2. The new cultivar has a uniform bright neon color with no variegation, while 'HUTAMT41' is usually solid green, which may show minor lighter areas.
3. Leaves of the new cultivar are heart-shaped and develop fenestrations slightly earlier, whereas 'HUTAMT41' leaves are thicker and fenestrate later.
4. The new cultivar is bushier with a more horizontal leaf orientation, while 'HUTAMT41' grows slightly upright and compact.
5. Petioles of the new cultivar are thinner and brightly colored, whereas 'HUTAMT41' petioles are thicker and green.

BRIEF DESCRIPTION OF THE PHOTOGRAPH

The accompanying photograph illustrates in full color a typical plant of the new cultivar 'LONGPRIDEMO01' grown in a greenhouse in Gaoshu Township, Taiwan. The plant is approximately 3 months old in a 6-inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 6$^{th}$ Edition 2015 except where general terms of ordinary dictionary significance are used. The following observations and measurements describe 'LONGPRIDEMO01' plants grown in a greenhouse in Gaoshu Township, Taiwan. The growing temperature ranged from approximately 20° C. to 28° C. during the day and from approximately 18° C. to 22° C. during the night. General light conditions are normal sunlight and numerical values represent averages of typical plant types.

Botanical classification: *Monstera deliciosa* 'LONGPRIDEMO01'.

PROPAGATION

Typical method: Tissue culture.

Root description: Fleshy roots. Roots approximately 4 to 8 mm in diameter. Colored Orange-White 159D.

PLANT

Growth habit: Upright tender perennial which spreads horizontally after 6 to 8 months. Basal leaves emerge in a slightly irregular rosette.

Plant shape: Upright, petioles and leaves slightly arching out. No stems.

Height: Approximately 30 cm to top of foliar plane.

Plant spread: Approximately 35 cm in a 6 inch pot.

Pot size of plant described: 6 inch.

Growth rate: Rapid. 8 inch finished pot is ready after about 6 months.

Branching characteristics: No true branching. Leaves emerge directly from base of plant.

Age of plant described: Approximately 4 months.

FOLIAGE

Leaf:

*Arrangement*.—Single leaves emerging basally in an irregular rosette.

*Largest, mature, fully expanded leaf*.—

*Length* (*excluding petiole*).—Overall 25 to 30 cm. Length from petiole attachment to apex; 15 to 20 cm.

*Width*.—20 to 25 cm.

*Shape of blade*.—Cordate.

*Aspect*.—Very slightly undulating, mainly flat.

*Apex*.—Acute.

*Base*.—Cordate, deep lobes, about 6 to 7 cm deep.

*Margin*.—Entire with deep lobes in a symmetrical pattern. Young foliage entire, no lobes.

*Lobes*.—2 to 3 deep lobes on each side of the leaf, usually symmetrical with maturity. Lobes 5 cm to 10 cm deep and 8 to 14 mm wide. Narrow oblong in shape, lobe margins entire.

*Appearance*.—Upper surface glossy. Lower surface glossy.

*Texture of top surface*.—Glabrous.

*Texture of bottom surface*.—Glabrous.

*Color*.—Immature foliage upper side: Yellow-Green N144B with overlay Green-Yellow 1A. Immature foliage under side: Green 143B. Mature foliage upper side: Green 143C with overlay Yellow-Green 150C. Mature foliage under side: Green 143B.

Venation:

*Type*.—Pinnate.

*Venation coloration upper side mature foliage*.—Yellow-Green 144D.

*Venation coloration under side mature foliage*.—Green 139D.

Petiole:

*Length*.—Average range between 15 and 19 cm.

*Width*.—At base: Approximately 1 cm, excluding petiole wing. At leaf attachment: Approximately 6 mm. Color: Green 143B.

*Strength*.—Very strong.

*Texture*.—Glabrous.

*Petiole wing*.—Length: Average range between 4 and 6 cm. Width: 9 mm at lowermost; 3 mm at uppermost. Color: Yellow-Green 154C. Texture: Glabrous all surfaces.

FLOWER

Not observed.

REPRODUCTIVE ORGANS

Not observed.

OTHER CHARACTERISTICS

Fruits and seeds: Not observed to date.

Disease/pest resistance: Neither resistance nor susceptibility to other normal diseases and pests of *Monstera* observed.

Temperature range: USDA zones 9 to 11.

What is claimed is:

1. A new and distinct cultivar of *Monstera* plant named 'LONGPRIDEMO01' as herein illustrated and described.

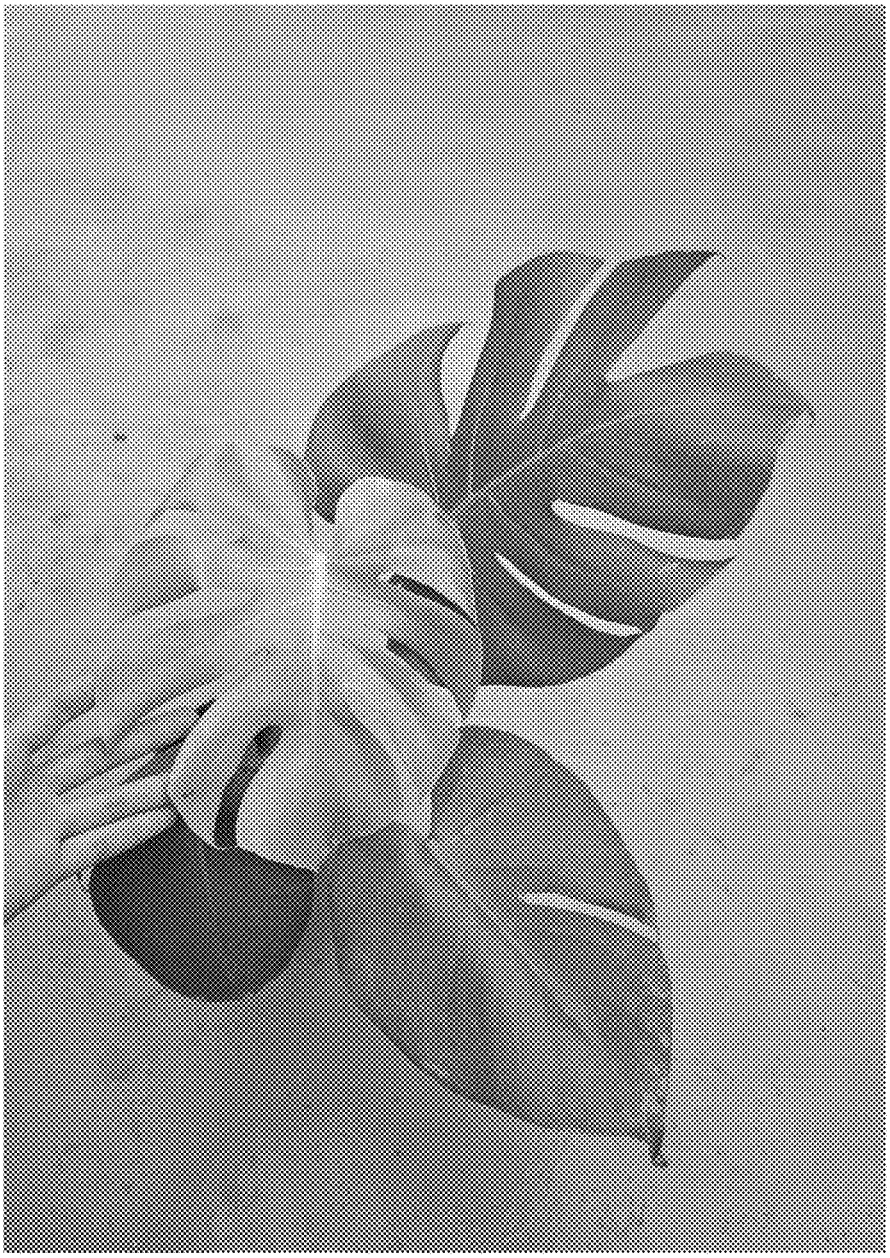

* * * * *